US012557886B2

(12) United States Patent
Min et al.

(10) Patent No.: US 12,557,886 B2
(45) **Date of Patent: *Feb. 24, 2026**

(54) RING-TYPE WEARABLE DEVICE

(71) Applicant: SAMSUNG ELECTRONICS CO., LTD., Suwon-si (KR)

(72) Inventors: Jin-hong Min, Suwon-si (KR); Jea-hyuck Lee, Anyang-si (KR); Seong-wook Jo, Suwon-si (KR); Shin-hee Cho, Suwon-si (KR); Su-ho Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 196 days.

This patent is subject to a terminal disclaimer.

(21) Appl. No.: 18/416,655

(22) Filed: Jan. 18, 2024

(65) Prior Publication Data

US 2024/0156218 A1      May 16, 2024

Related U.S. Application Data

(63) Continuation of application No. 17/738,680, filed on May 6, 2022, now Pat. No. 11,963,590, which is a (Continued)

(30) Foreign Application Priority Data

Feb. 1, 2016    (KR) ........................ 10-2016-0012237

(51) Int. Cl.
*A61B 5/1455*      (2006.01)
*A44C 9/00*        (2006.01)
(Continued)

(52) U.S. Cl.
CPC .......... *A44C 9/0053* (2013.01); *A44C 9/0023* (2013.01); *A44C 15/0015* (2013.01); (Continued)

(58) Field of Classification Search
CPC ... A61B 5/0006; A61B 5/0059; A61B 5/0205; A61B 5/24; A61B 5/02416; (Continued)

(56) References Cited

U.S. PATENT DOCUMENTS 5,746,206 A      5/1998  Mannheimer
5,964,701 A      10/1999 Asada et al.
(Continued)

FOREIGN PATENT DOCUMENTS

JP      2007-054497      3/2007
JP      2008-188215      8/2008
(Continued)

OTHER PUBLICATIONS

International Search Report for PCT/KR2016/012432, mailed Feb. 14, 2017, 4 pages.
(Continued)

*Primary Examiner* — Chu Chuan Liu
(74) *Attorney, Agent, or Firm* — Nixon & Vanderhye, P.C.

(57) ABSTRACT
A ring-type wearable device is disclosed. The disclosed ring-type wearable device comprises: an outer ring member; an inner ring member separably inserted into the outer ring member; a sensor unit disposed in the outer ring member; and a control unit disposed in the outer ring member so as to be electrically connected to the sensor unit, wherein the sensor unit can maintain constant sensitivity in correspondence to the thickness of the inner ring member.

24 Claims, 20 Drawing Sheets

Related U.S. Application Data continuation of application No. 16/070,379, filed as application No. PCT/KR2016/012432 on Nov. 1, 2016, now Pat. No. 11,324,292.

(51) Int. Cl.

| | |
|---|---|
| *A44C 15/00* | (2006.01) |
| *A61B 5/00* | (2006.01) |
| *A61B 5/024* | (2006.01) |
| *A61B 5/24* | (2021.01) |

(52) U.S. Cl.
CPC .......... *A61B 5/0006* (2013.01); *A61B 5/0059* (2013.01); *A61B 5/02416* (2013.01); *A61B 5/02438* (2013.01); *A61B 5/24* (2021.01); *A61B 5/6826* (2013.01); *A61B 2560/0468* (2013.01)

(58) Field of Classification Search
CPC .............. A61B 5/02438; A61B 5/1455; A61B 5/14551; A61B 5/14552; A61B 5/6814; A61B 5/6822; A61B 5/6824; A61B 5/6826

See application file for complete search history.

(56) References Cited

U.S. PATENT DOCUMENTS

| | | | |
|---|---|---|---|
| 6,402,690 | B1 | 6/2002 | Rhee |
| 10,429,888 | B2 | 10/2019 | Connor |
| 10,433,172 | B2 | 10/2019 | Seo et al. |
| 11,134,381 | B2 | 9/2021 | Seo et al. |
| 11,324,292 | B2 | 5/2022 | Min et al. |
| 2002/0169381 | A1 | 11/2002 | Asada |
| 2007/0060807 | A1 | 3/2007 | Oishi |
| 2008/0275309 | A1 | 11/2008 | Stivoric |
| 2011/0007035 | A1 | 1/2011 | Shai |
| 2011/0210931 | A1 | 9/2011 | Shai |
| 2012/0165632 | A1 | 6/2012 | Baker, Jr. |
| 2012/0218184 | A1 | 8/2012 | Wissmar |
| 2013/0091895 | A1 | 4/2013 | Hwang |
| 2014/0053604 | A1 | 2/2014 | Newton et al. |
| 2015/0065090 | A1 | 3/2015 | Yeh |
| 2015/0119654 | A1 | 4/2015 | Martin |
| 2015/0220109 | A1 | 8/2015 | Von Badinski |
| 2015/0220922 | A1 | 8/2015 | Elangoven et al. |
| 2015/0277559 | A1 | 10/2015 | Vescovi et al. |
| 2017/0071483 | A1* | 3/2017 | Wang ................. A61B 5/14551 |
| 2019/0268771 | A1 | 8/2019 | Seo et al. |
| 2020/0029216 | A1 | 1/2020 | Seo et al. |

FOREIGN PATENT DOCUMENTS

| | | |
|---|---|---|
| KR | 10-2000-0052757 | 8/2000 |
| KR | 20-0431839 | 11/2006 |
| KR | 10-2007-0081608 | 8/2007 |
| KR | 10-0906826 | 7/2009 |
| KR | 10-2009-0102264 | 9/2009 |
| KR | 10-2010-0066728 | 6/2010 |
| KR | 10-2010-0072198 | 6/2010 |
| KR | 10-2014-0074824 | 6/2014 |
| KR | 10-2014-0102403 | 8/2014 |
| WO | 03/025734 | 3/2003 |
| WO | 2015/129556 | 9/2015 |
| WO | 2015-153803 | 10/2015 |

OTHER PUBLICATIONS

Written Opinion of the ISA for PCT/KR2016/012432, with English translation, mailed Feb. 14, 2017, 8 pages.

Novel Wearable and Wireless Ring-Type Pulse Oximeter with Multi-Detectors, Sensors 2014, pp. 17586-17599.

Extended Search Report mailed Dec. 4, 2018 in counterpart European Application No. 16889528.2.

Notice of Preliminary Rejection dated Feb. 23, 2022 in Korean Patent Application No. 10-2016-0012237 and English-language translation.

Min et al., U.S. Appl. No. 16/070,379, filed Jul. 16, 2018, now U.S. Pat. No. 11,324,292.

Min et al., U.S. Appl. No. 17/738,680, filed May 6, 2022, allowed.

\* cited by examiner

100'

110'

130'

RING-TYPE WEARABLE DEVICE

CROSS-REFERENCE TO RELATED APPLICATIONS

This application is continuation of U.S. application Ser. No. 17/738,680, filed 6 May 2022, which is a continuation of U.S. application Ser. No. 16/070,379, filed 16 Jul. 2018, now U.S. Pat. No. 11,324,292, which is the U.S. national phase of International Application No. PCT/KR2016/012432 filed 1 Nov. 2016, which designated the U.S. and claims priority to KR Patent Application No. 10-2016-0012237 filed 1 Feb. 2016. The entire contents of each of these applications are hereby incorporated by reference in their entireties.

FIELD

The present disclosure relates to a ring-type wearable device, and more particularly, to a ring-type wearable device capable of detecting a biological signal of a user.

DESCRIPTION OF RELATED ART

In general, a wearable device is an electronic device which can be freely worn in a body and carried out such as clothes, watches, and glasses. Such a wearable device includes smart glasses, a smart watch, a ring-type wearable device, and the like.

Since thicknesses of fingers of the users are different from each other, the ring-type wearable device is manufactured to have a size suitable for the finger of each of the users. However, general rings are divided in serval tens of sizes (for example, 27 sizes in Korea and 65 sizes in USA). When the wearable device is also divided into several sizes according to division of the ring, the design of the wearable device is changed according to the corresponding size and thus the cost is considerably increased.

The positions of skin detection sensors provided in the ring-type wearable devices are differently controlled according to corresponding sizes of the ring-type wearable devices. Due to this, it is difficult to constantly maintain a distance between the skin and the sensor with respect to all the sizes of the ring-type wearable devices and to guarantee the uniform quality of the measured signals according to the sizes.

SUMMARY

The object of the present invention is to provide a ring-type wearable device capable of corresponding to fingers sizes of the users having various thicknesses by combining an outer ring member and an inner ring member and constantly maintaining sensitivity of a sensing unit even in change of the size of the device.

To achieve the above-described object, the present invention provides a ring-type wearable device including an outer ring member; an inner ring member detachably inserted into an inner side of the outer ring member; a sensor unit disposed in the outer ring member; and a control unit disposed in the outer ring member and electrically coupled to the sensor unit. The sensor unit maintains constant sensitivity with respect to a thickness of the inner ring member.

The sensor unit may be a photo sensor including a light-emitting part and a light-receiving part configured to receive light emitted from the light-emitting part and reflected from an inside of a finger.

The inner ring member may include a lens configured to control a light radiation distance of the light-emitting part and the lens may be disposed in a position corresponding to the light-emitting part and have the same thickness as that of the inner ring member.

The light-emitting part may be elastically supported to the outer ring member in a state that the light-emitting part is inserted into a through hole formed in the inner ring member and a position of the light-emitting part may be varied according to a thickness of the inner ring member.

The ring-type wearable device may further include a cover member which surrounds an outer side of the outer ring member and the light-emitting part may be elastically supported to the cover member and a position of the light-emitting part may be varied according to a thickness of the inner ring member.

The ring-type wearable device may further include a fixed resistor having a resistance value corresponding to a corresponding thickness of the inner ring member; and a resistance measurement circuit configured to detect the resistance value of the fixed resistor. The control unit may control a light-emitting intensity of the light-emitting part corresponding to the resistance value detected through the resistance measurement circuit.

The light-emitting part may have a first light-emitting amount with respect to a first thickness of the inner ring member and have a second light-emitting amount larger than the first light-emitting amount with respect to a second thickness of the inner ring member larger than the first thickness of the inner ring member.

The sensor unit may further include a galvanic skin response (GSR) sensor; and an electrocardiogram (ECG) sensor and the inner ring member may include a skin contact terminal electrically coupled to a terminal of the GSR sensor. A first terminal of the ECG sensor may be exposed toward an inner side of the inner ring member and a second terminal thereof may be exposed toward an outer side of the outer ring member.

The ring-type wearable device may further include a display unit disposed in the outer ring member and a dial member rotatably coupled to an outer side of the outer ring member and configured to operate the display unit.

The display unit may be disposed to a circumferential direction along at least one side surface of the outer ring member.

The display unit may include first and second display units disposed to a circumferential direction along both side surfaces of the outer ring member on the basis of the dial member and information displayed in the first and second display units may be switched to each other.

The dial member may include a rotating body which rotates to forward and reverse directions; a magnetic body which rotates with the rotating body and has N poles and S poles alternately arranged; and a hall sensor configured to detect polarity change of a magnetic pole to the magnetic body according to rotation of the rotating body. The control unit may calculate a rotation amount of the rotating body through a sensing signal detected through the hall sensor.

The dial member may include a rotating body which rotates to forward and reverse directions; a plurality of reflectors which rotate with the rotating body and are arranged at intervals; and an image sensor configured to receive light reflected from the plurality of reflectors according to rotation of the rotating body. The control unit may calculate a rotation amount of the rotating body through a sensing signal detected through the image sensor.

The dial member may include a rotating body which rotates to forward and reverse directions; a plurality of protrusions formed to protrude at intervals along an inner side of the rotating body; and a switch operated through the plurality of protrusions according to rotation of the rotating body. The control unit may calculate a rotation amount of the rotating body through a sensing signal detected through the switch.

The ring-type wearable device may further include a cover member which surrounds an outer periphery of the outer ring member. An antenna connected to a wireless communication module provided in the outer ring member may be disposed in an inner side of the cover member and the antenna may be configured of a non-metal material to transmit and receive signals to and from the external apparatus.

DETAILED DESCRIPTION OF EXAMPLE EMBODIMENTS

Figure 1:
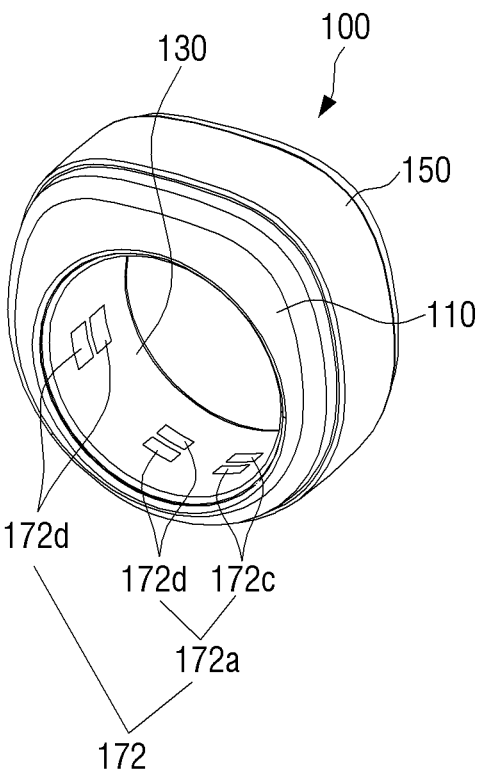
FIG. 1 is an assembled perspective view illustrating a ring-type wearable device according to an embodiment of the present invention.

Hereinafter, various embodiments of the disclosure will be described more fully with reference to the accompanying drawings. However, in the following description, it is understood that the technology described therein may not be limited to a specific embodiment, and various modifications, equivalents, and/or alternatives of the embodiments may be included therein without departing from the principles and spirit of the present disclosure. In the following description, unless otherwise described, the same reference numerals are used for the same elements when they are depicted in different drawings.

It will be understood that, although the terms "first", "second", etc. may be used herein in reference to elements of the invention regardless of an order and/or importance, such elements should not be construed as limited by these terms. The terms are used only to distinguish one element from other elements. For example, 'a first portion' and 'a second portion' may refer to different portions regardless of an order or importance. For example, without departing from the spirit of the inventive concept, a first element may refer to a second element, and similarly, the second element may refer to the first element.

The terminology used herein is for the purpose of describing particular embodiments only and is not intended to be limiting of the invention. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, even the terms defined in the present disclosure should not be construed as excluding the exemplary embodiments of the present disclosure.

A ring-type wearable device disclosed in the present disclosure may detect a biological signal of the user through various types of sensors provided therein, analyze the detected biological signal, wirelessly transmit analysis data such as pulse, sleep level, blood pressure, and the like to a preset external device (for example, a mobile device having a display, a monitor, a television (TV), and the like), and display the analysis data. Further, the ring-type wearable device disclosed in the present disclosure may include its own display and may display various user interfaces (UIs), for example, a menu for selecting various functions and information displayed according to execution of a corresponding function in figures, image, and the like through the display.

Hereinafter, a configuration of a ring-type wearable device according to an embodiment of the present invention will be described in detail with reference to the accompanying drawings.

Figure 2:
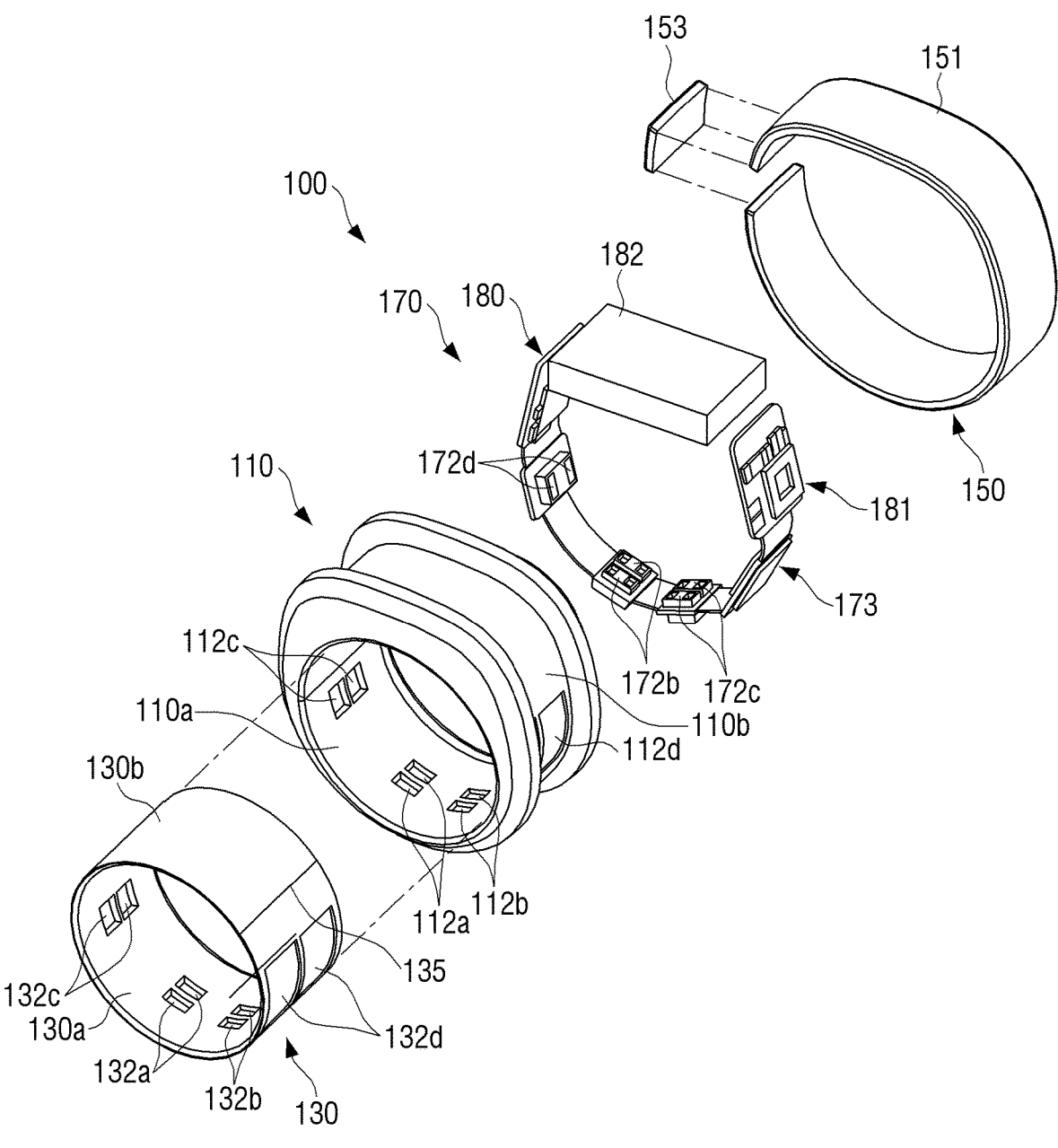
FIG. 2 is an exploded perspective view illustrating a ring-type wearable device according to an embodiment of the present invention.
Figure 3:
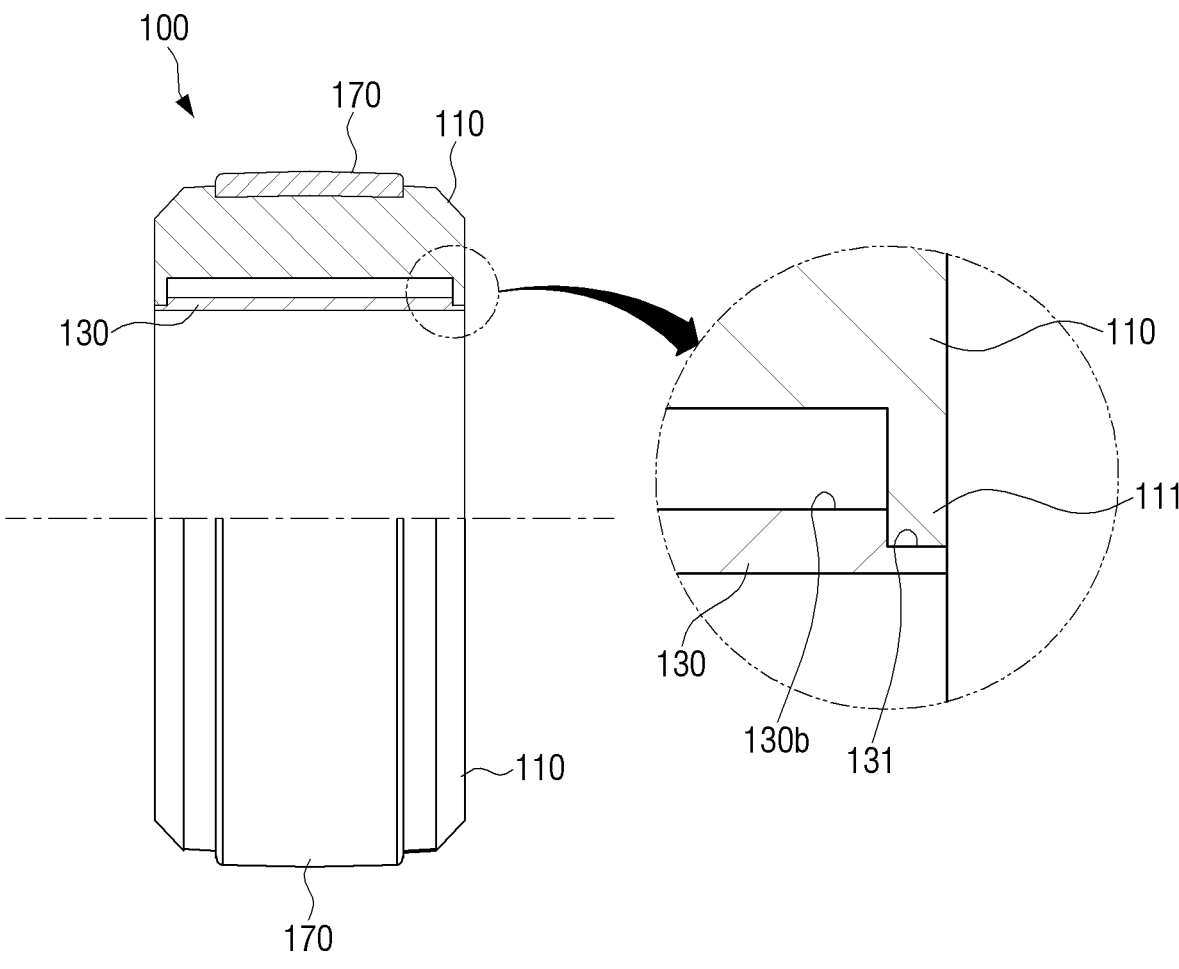
FIG. 3 is a partially broken sectional view illustrating a coupling structure of an outer ring member and an inner ring member.

FIG. 1 is an assembled perspective view illustrating a ring-type wearable device according to an embodiment of the present invention, FIG. 2 is an exploded perspective view illustrating a ring-type wearable device according to an embodiment of the present invention, and FIG. 3 is a partially broken sectional view illustrating a coupling structure of an outer ring member and an inner ring member.

Referring to FIGS. 1 and 2, a ring-type wearable device 100 according to an embodiment of the present invention may include an outer ring member 110, an inner ring member 130 disposed along an inner circumferential surface of the outer ring member 110, a cover member 150 disposed along an outer periphery of the outer ring member 110, and a circuit unit 170 installed in the outer ring member 110.

The outer ring member 110 may have an inner diameter sufficient to be fitted to the finger of the user. In this case, since the finger of the user is in direct contact with the inner ring member 130, the inner diameter of the outer ring member 110 may be manufactured in consideration of a thickness of the inner ring member 130. The outer ring member 110 may be manufactured in various sizes to correspond to an age, a gender, and the like in consideration of various finger thicknesses of a plurality of users. For example, the outer ring member 110 may be provided in at least three different sizes. That is, when the smallest size of the outer ring member 110 is A1, the outer ring members 110 may be divided into A1, A2, and A3 (A1<A2<A3).

In this regard, the inner ring member 130 may be manufactured in a size applicable to the outer ring members 110 having the different sizes of A1, A2, and A3. That is, the inner ring member 130 may be manufactured in sizes of B1-1, B1-2, and B1-3 (B1-1<B1-2<B1-3) applicable to the outer ring member having the A1 size, the inner ring member 130 may be manufactured in sizes of B2-1, B2-2, and B2-3 (B2-1<B2-2<B2-3) applicable to the outer ring member having the A2 size, and the inner ring member 130 may be manufactured in sizes of B3-1, B3-2, and B3-3 (B3-1<B3-2<B3-3) applicable to the outer ring member having the A3 size. Although it is described in the embodiment that the outer ring member 110 is provided in three sizes and the inner ring member 130 is provided in three sizes with respect to each of the sizes of the outer ring members 110, this is not limited thereto. The outer ring member 110 and the inner ring member 130 are configured in various sizes and thus the numbers of sizes of the outer ring member 110 and the inner ring member may be provided larger or smaller than three described in the embodiment.

Referring to FIG. 3, the inner ring member 130 may be detachably coupled along an inner circumferential surface 110a of the outer ring member 110. In this case, a coupling protrusion 111 which protrudes by a predetermined length toward the center of the outer ring member 110 may be formed in an end portion of the inner circumferential surface 110a of the outer ring member 110. The coupling protrusion 111 of the outer ring member 110 may be placed in a coupling groove 131 formed along either end of an outer circumferential surface 130b of the inner ring member 130. The outer ring member 110 and the inner ring member 130 may be stably coupled to each other through a coupling structure of the outer ring member 110 and the inner ring member 130, that is, the coupling protrusion 111 and the coupling groove 131. In this case, other than the above-described coupling structure of the outer ring member 110 and the inner ring member 130, the inner ring member 110 may be attached to the outer ring member 110 through an adhesive or the inner ring member 130 is fixed to the outer ring member 110 through a separate fastening screw (not shown) and the like.

The outer ring member 110 may be formed with a groove in which the circuit unit 170 may be placed along an outer circumferential surface 110b. The outer ring member 110 may be formed with a plurality of openings 112a, 112b, 112c, and 112d to expose portions (LED, terminal, and the like) of various sensors included in the circuit unit 170, charge terminals, or the like toward an inner ring member 130 side. For example, a light-emitting part 172a of a photo-plethysmography (PPG) sensor 172 configured to measure blood oxygen saturation ($SpO_2$) may be exposed through the first and second openings 112a and 112b formed in pairs, the light-receiving part 172d of the PPG sensor 172 may be exposed through the pair of third openings 112c, and a skin contact terminal (see 173b of FIG. 13) of a galvanic skin response (GSR) sensor 173 may be exposed through the fourth opening 112d. Further, although not shown in drawings, the outer ring member 110 may be formed with an opening through which a terminal of an electrocardiogram (ECG) sensor may be exposed and an opening through which a charge terminal configured to charge a built-in battery 182 may be exposed.

Figure 4:
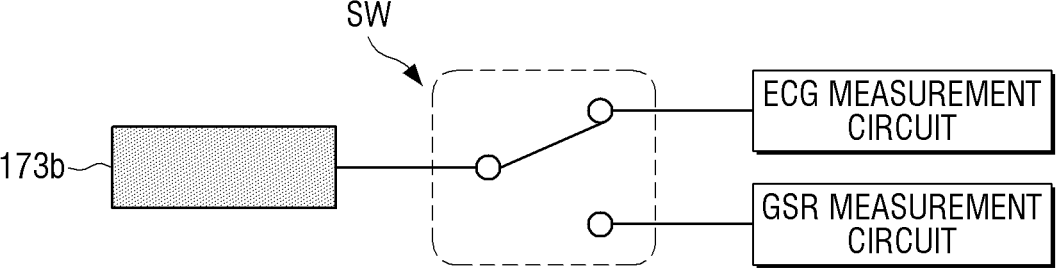
FIG. 4 is a schematic diagram illustrating an example that a terminal of a GSR sensor is commonly used in a GSR measurement circuit and an ECG measurement circuit.

Further, referring to FIG. 4, the terminal 173b of the GSR sensor 173 may also be used as the terminal of the ECG sensor. That is, the terminal 173b of the GSR sensor 173 may be implemented to be selectively coupled to any one of a GSR measurement circuit and an ECG measurement circuit by arranging a switching circuit SW (for example, analog switch IC, multiplexer, and the like) between the terminal 173b of the GSR sensor 173 and terminals of the GSR measurement circuit and the ECG measurement circuit. In this case, the user may transmit a select signal to the ring-type wearable device 100 through a predetermined UI displayed in an external device (see 20 of FIG. 13) and a control unit (see 185 of FIG. 8) of the ring-type wearable device may determine the select signal and couple the terminal 173b of the GSR sensor 173 to any one of the GSR measurement circuit and the ECG measurement circuit by driving the switching circuit SW.

The outer ring member 110 may be configured of a metal material. However, this is not limited thereto and the outer ring member 110 may be configured of a synthetic resin material and a metal coating layer or a non-metal coating layer capable of giving an impression of a metal material may be formed on a surface of the outer ring member 110. In this case, the inner ring member 130 and the cover member 150 may be formed of a metal material or a non-metal material capable of giving an impression of a metal material to be in harmony with the design of the outer ring member 110.

The outer ring member 110 is entirely ring-shaped, but a portion of the outer ring member 110 in which the battery 182 is located corresponds to a flat shape of the battery 182 and has a curvature different from that of a remaining portion of the outer ring member 110. However, the outer ring member 110 may have a regular shape as illustrated in FIG. 5 other than such a shape.

Figure 5:
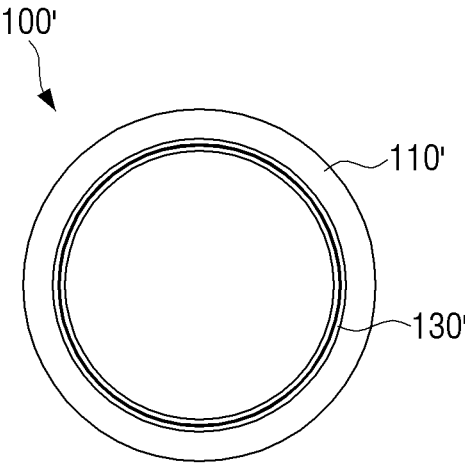
FIG. 5 is a diagram illustrating an example that an outer ring member has a regular circle.

FIG. 5 is a diagram illustrating an example that the outer ring member has a regular circle.

Referring to FIG. 5, an outer ring member 110' of a ring-type wearable device 100' may also be configured in a regular circle like an inner ring member 130'. In this case, a battery provided in the ring-type wearable device 100' may employ a flexible battery formed of a flexible material. Accordingly, the battery may be formed to have the same curvature as that of the outer ring member 110' or to have a similar curvature to that of the outer ring member 110'.

The inner ring member 130' may be configured in a circular shape and have a predetermined thickness. The inner ring member 130' may be detachably coupled along an inner circumferential surface of the outer ring member 110'. Since the inner ring member 130' is in direct contact with the finger skin of the user, the inner ring member 130' may be configured of a metal material or a non-metal material which does not cause skin troubles. When the inner ring member 130' is manufactured of the non-metal material, a coating layer may be formed on a surface of the inner ring member 130' to maintain the same color as that of the outer ring member 110'.

Figure 6:
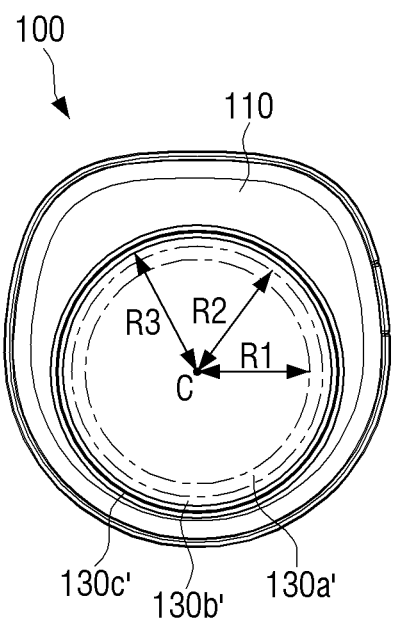
FIG. 6 is a diagram illustrating various thicknesses of an inner ring member coupled to an outer ring member.

FIG. 6 is a diagram illustrating various thicknesses of an inner ring member coupled to an outer ring member.

Referring to FIG. 6, the inner ring member 130 may be used, for example, by coupling at least one of inner ring members 130a', 130b', and 130'c having the sizes of B1-1, B1-2, and B1-3 having different inner diameters from each other to the outer ring member 110 having the size of A1. In this case, the inner ring member 130a', 130b', and 130c' having the sizes of B1-1, B1-2, and B1-3 may have radii of R1, R2, and R3 (R1<R2<R3). The reference numeral "C" illustrated in FIG. 5 indicates the centers of the inner ring members 130a', 130b', and 130c'. The inner ring members 130a', 130b', and 130c' having the different inner diameters from each other may be configured to have the same outer diameter as each other to be coupled to the outer ring members 110 having the same size.

Referring back to FIG. 2, the inner ring member 130 may be formed with openings 132a, 132b, 132c, and 132d corresponding to the plurality of openings 112a, 112b, 112c, and 112d of the outer ring member 110. Accordingly, portions (LED, terminal, and the like) of the various types of sensors included in the circuit unit 170, a charge terminal, and the like may be exposed toward the finger side through the outer ring member 110 and the inner ring member 130.

The inner ring member 130 may be formed with a cutting portion 135 in a portion thereof to be easily inserted along the inner circumferential surface of the outer ring member 110. The shape of the inner ring member 130 may be modified when external power is applied to the inner ring member 130 by the cutting portion 135. That is, when pressure is applied to the inner ring member 130, the inner ring member 130 may be shrunk and the diameter of the inner ring member 130 may be temporarily reduced. In the state that the diameter of the inner ring member is reduced, the inner ring member 130 may be inserted along the inner circumferential surface 110a of the outer ring member 110. When the inner ring member 130 is inserted and then the pressure applied to the inner ring member 130 is removed, the inner ring member 130 may be restored to a circular shape through its own elasticity and thus the inner ring member 130 may be stably coupled to the inner circumferential surface 110a of the outer ring member 110. Further, although not shown in the drawings, the inner ring member 130 may be formed to be divided into two portions. In this case, the two portions constituting the inner ring member 130 may be fixed to the inner circumferential surface 110a of the outer ring member 110 through an adhesive or a fastening piece.

The cover member 150 is coupled to an outer side of the outer ring member 110 in a state that the circuit member 170 is covered with the cover member 150 so as not to expose the circuit unit 170 and the battery 182 installed in the outer circumferential surface 110b of the outer ring member 110. In this case, the cover member 150 may be coupled to the outer ring member 110 through an adhesive or a fastening piece.

The cover member 150 may include a first part 151 and a second part 153. The first part 151 is configured in a shape corresponding to an outer periphery of the outer ring member 110 and covers most of the outer side of the outer ring member 110. The second part 153 may be disposed in a position corresponding to a switch 183 of the circuit unit 170. The second part 153 may be installed in the outer ring member 110 to cover the switch 183 and simultaneously to press a button (see 183a of FIG. 7(B)) of the switch 183 in a state that the second part 153 is separated from the first part 151.

The cover member 150 may be entirely configured of a metal material or a non-metal material. So as not to interfere with transmission and reception of a wireless signal of an antenna (not shown) electrically coupled to a communication module 181 of the circuit unit 170, a portion of the cover member 150 corresponding to the antenna may be configured of a non-metal material or the cover member 150 may be entirely configured of a non-metal material. The antenna may be disposed in the outer ring member 110 or an inner circumferential surface of the cover member 150.

Figure 7A:
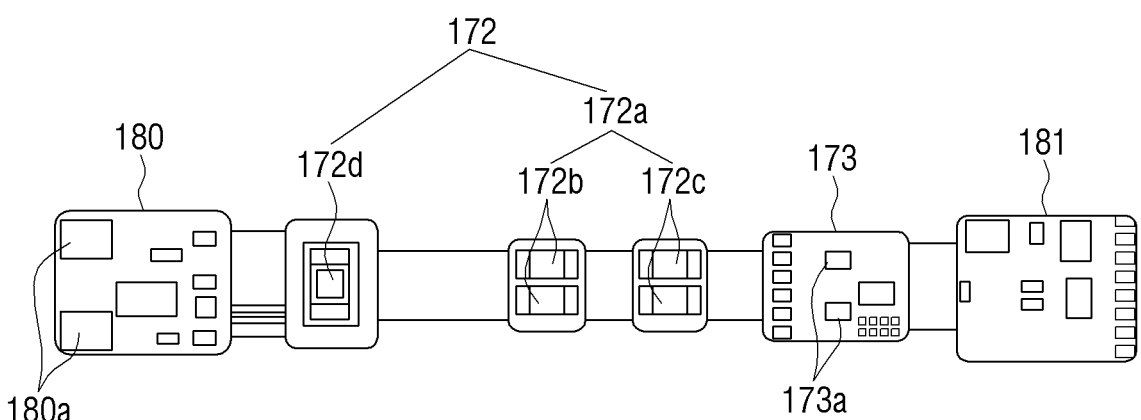
FIGS. 7A and 7B are diagrams illustrating a top and a bottom of a circuit unit.
Figure 7B:
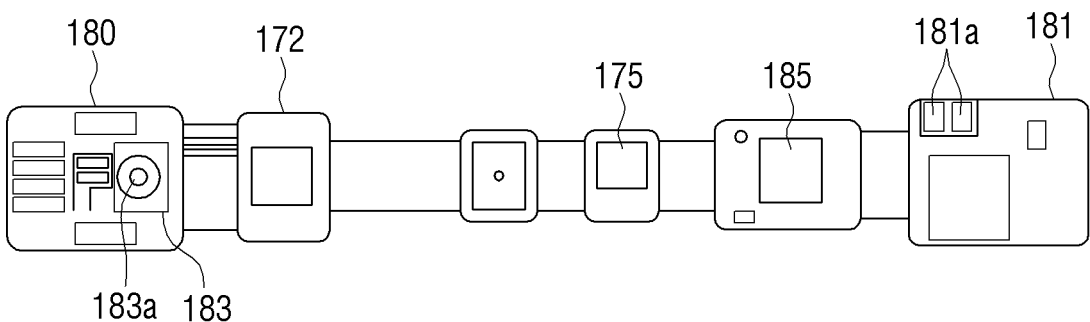
Figure 8:
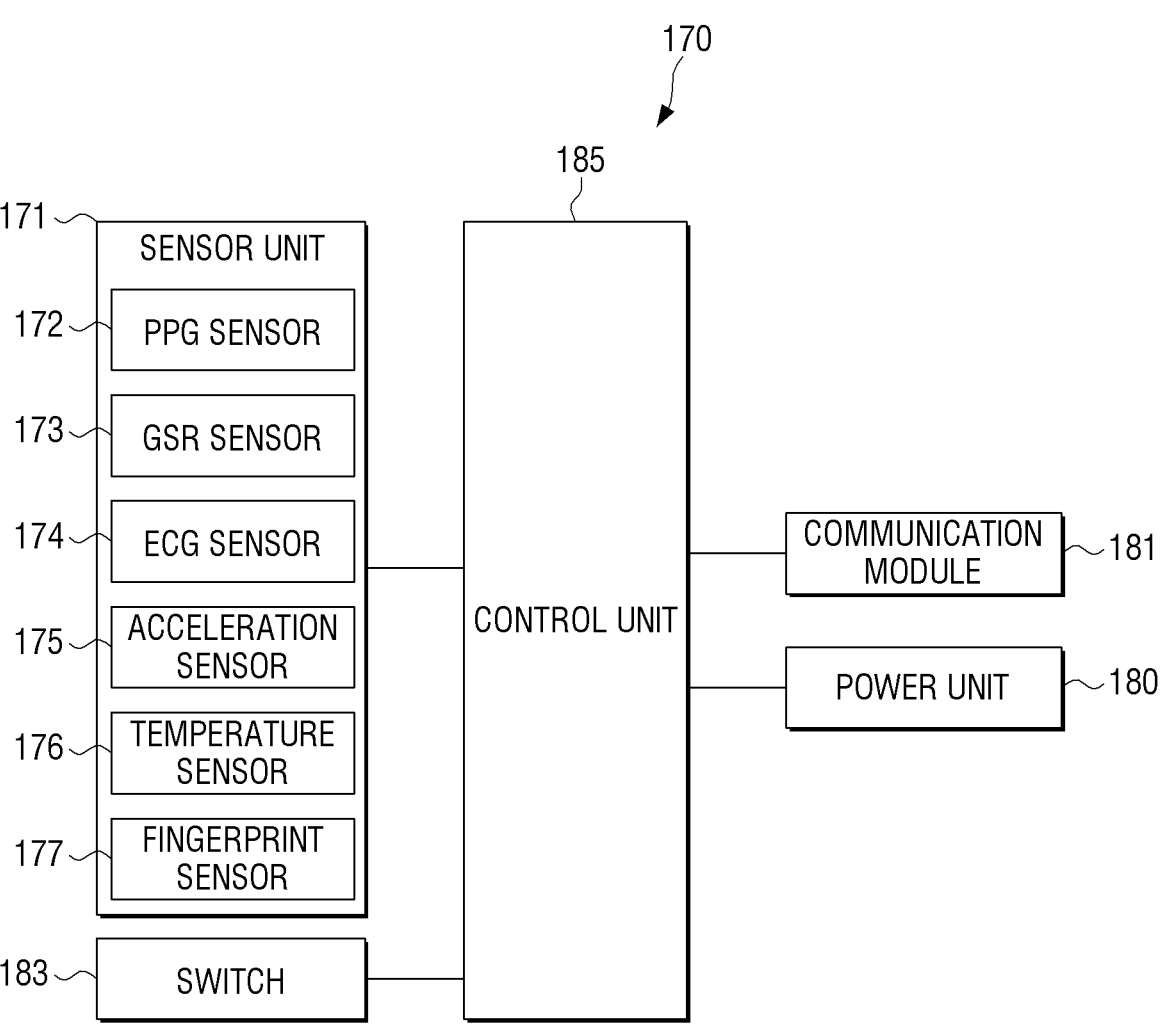
FIG. 8 is a block diagram illustrating a state that a sensor unit, a power unit, a communication module, and a switch are electrically coupled to a control unit.

FIG. 7 is a diagram illustrating a top and a bottom of a circuit unit and FIG. 8 is a block diagram illustrating a state that a sensor unit, a power unit, a communication module, and a switch are electrically coupled to a control unit.

Referring to FIGS. 7(A) and (B), the circuit unit 170 may include a sensor unit 171, a power unit 180, the communication module 181, the switch 183, and the control unit 185. The circuit unit 170 may include a plurality of printed circuit boards (PCBs), various types of sensors and elements mounted on the PCBs, and a flexible printed circuit board (FPCB) configured to electrically couple the plurality of PCBs arranged in a row to each other.

The sensor unit 171 may perform various functions as follows. The sensor unit 171 may perform a function of detecting apnea in the user's sleep, a function of detecting sleeping and sleeping step, a function of detecting drowsiness, a function of measuring blood pressure, a function of measuring calorie consumption, a function of measuring a skin hydration, a function of authenticating the user, and a function of measuring temperature.

Referring to FIG. 8, the sensor unit 171 may include various sensors, for example, the PPG sensor 172, the GSR sensor 173, an ECG sensor 174, an acceleration sensor 175, a temperature sensor 176, and a fingerprint sensor 177 to perform the above-described various functions. Hereinafter, the sensors configured to perform the functions which may be implemented through the sensor unit 171 will be described.

The PPG sensor 172 may measure the blood oxygen saturation to detect the apnea in the user's sleep. The PPG sensor 172 may include the light-emitting part 172a configured to emit light toward the finger and the light-receiving part 172d configured to receive the light emitted from the light-emitting part 172a and reflected to the blood vessel inside the finger as illustrated in FIG. 7(A).

The light-emitting part 172a may include first and second light sources 172b and 172c. The first light source 172b may be at least two or more red light emitting diodes (LEDs) and the second light source 172c may be at least two or more infrared LEDs. In this case, the light-emitting part 172a may also include a plurality of red LEDs and a plurality of infrared LEDs to improve the sensing performance of blood oxygen saturation of the finger.

The light-receiving part 172*d* may be one photodiode. The light-receiving part 172*d* may be disposed at a predetermined angle with respect to the light-emitting part 172*a* as illustrated in FIG. 1. For example, the light-receiving part 172*d* may be disposed at an angle of about 60 degrees with respect to the first light source 172*b* and disposed at an angle of about 95 degrees with respect to the second light source 172*c*. However, this is not limited thereto and the light-receiving part 172*d* may be disposed at various angles with respect to the first and second light sources 172*b* and 172*c*.

FIG. 9 is a cross-sectional diagram illustrating a structure for correcting sensing performance of a PPG sensor by providing different lenses according to a thickness of an inner ring member.

Figure 9A:
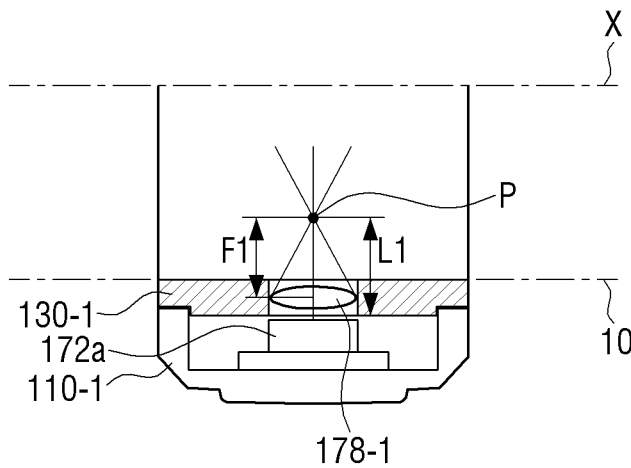
FIGS. 9A and 9B are cross-sectional diagrams illustrating a structure for correcting sensing performance of a PPG sensor by providing different lenses according to a thickness of an inner ring member.

Further, even when the inner ring members 130-1 and 130-2 having the different thicknesses from each other are used with respect to the outer ring members 110-1 having the same size, the sensing performance of the PPG sensor 172 may be adjusted through lenses 178-1 and 178-2 as illustrated in FIGS. 9(A) and (B).

Figure 9B:
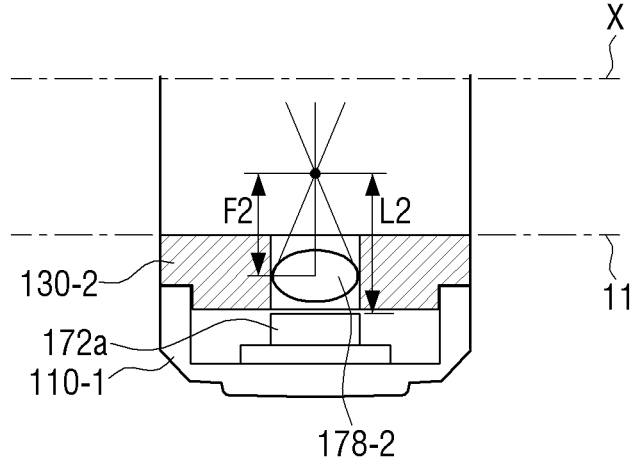

When it is assumed that a thickness of a finger 10 in FIG. 9(A) is larger than that of a finger 11 in FIG. 9(B), the inner ring member 130-1 of FIG. 9(A) may have the larger size than the inner ring member 130-2 of FIG. 9(B) with respect to the outer ring members 110-1 having the same size as each other. That is, the inner ring member 130-1 of FIG. 9(A) may have a larger inner diameter than the inner ring member 130-2 of FIG. 9(B).

In this case, a light radiation distance L1 between the light-emitting part 172*a* of FIG. 9(A) and an arbitrary position P inside the finger 10 may be smaller than a light radiation distance L2 between the light-emitting part 172*a* of FIG. 9(B) and an arbitrary position P inside the finger 11. Accordingly, the lens 178-2 of FIG. 9(B) may have the larger thickness than the lens 178-1 of FIG. 9(A) to set a focal length F2 of the lens 178-2 in FIG. 9(B) larger than a focal length F1 of the lens 178-1 in FIG. 9(A). Therefore, the sensing performance according to a difference between the light radiation distances L1 and L2 may be corrected in the embodiment.

Further, when the lens is provided to adjust the focal length of the light as illustrated in FIG. 9, a filter (not shown) configured to pass only a predetermined wavelength band and filter a remaining wavelength band may be provided in a font end or a rear end of the lens to emit or receive only the light having a preset wavelength.

FIG. 10 is a cross-sectional diagram illustrating an example that a position of a light-emitting part of a PPG sensor can be varied according to a thickness of an inner ring member.

Referring to FIG. 10, the light-emitting part 172*a* may be elastically supported to an outer ring member 110-4 through an elastic member 179 (for example, coil spring). One end of the elastic member 179 may support a rear end of the light-emitting part 172*a* and the other end of the elastic member 179 may be fixed to a fixing protrusion 179*a* formed to protrude in the outer ring member 110-4. In this case, the fixing protrusion 179*a* may be formed in the inner side of the cover member 150 other than the outer ring member 110-4.

Figure 10A:
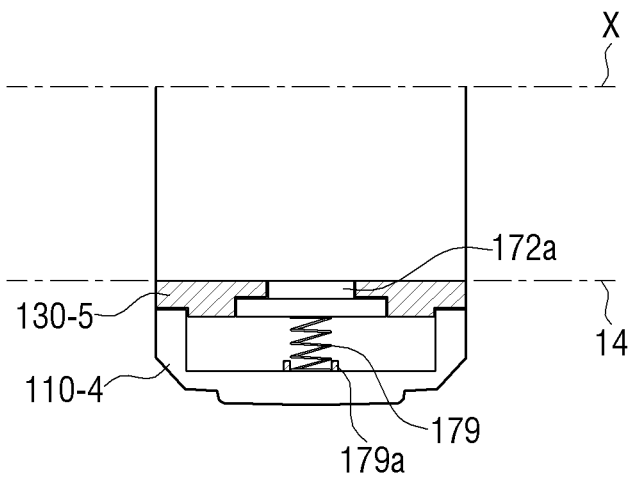
FIGS. 10A and 10B are cross-sectional diagrams illustrating an example that a position of a light-emitting part of a PPG sensor can be varied according to a thickness of an inner ring member.
Figure 10B:
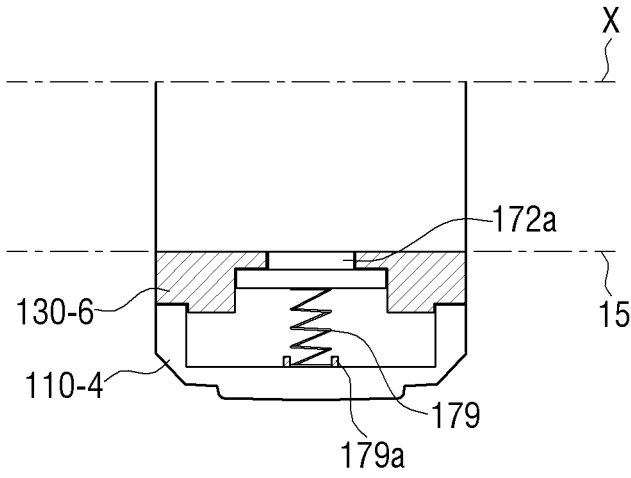

On the other hand, when it is assumed that a thickness of a finger 14 in FIG. 10(A) is larger than that of a finger 15 in FIG. 10(B) and the sizes of the outer ring members 110-4 are the same as each other, an inner diameter of an inner ring member 130-5 in FIG. 10(A) may be formed to be larger than that of an inner ring member 130-6 in FIG. 10(B).

In this case, the light-emitting part 172*a* of FIG. 10(A) may be disposed to be in contact with or to be close to a surface of the finger 14 through the elastic member 179 and the light-emitting part 172*a* of FIG. 10(B) may also be disposed to be in contact with or to be close to a surface of the finger 15 through the elastic member 179. Accordingly, a distance between the light-emitting part 172*a* and the skin may be uniformly kept all the times through elastic force of the elastic member 179 regardless of the inner diameters (or thicknesses) of the inner ring members 130-5 and 130-6.

FIG. 11 is a schematic diagram illustrating an example that different resistance values according to a thickness of an inner ring member are given and an intensity of a light-emitting part of a PPG sensor is differently controlled according to the different resistance values.

Figure 11A:
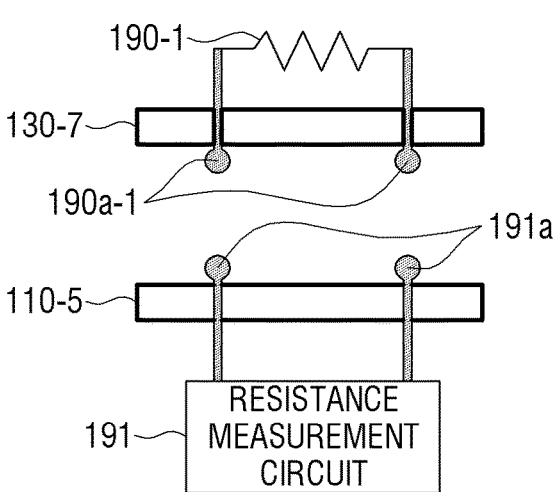
FIGS. 11A and 11B are schematic diagrams illustrating an example of controlling an intensity of a light-emitting part of a PPG sensor by detecting different resistance values according to a thickness of an inner ring member.
Figure 11B:
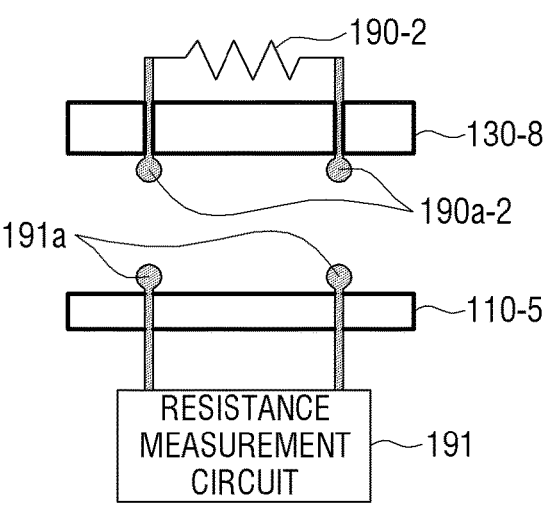

Referring to FIGS. 11(A) and (B), inner ring members 130-7 and 130-8 may include fixed resistors 190-1 and 190-2 having difference resistance values from each other with respect to sizes (thicknesses or inner diameters) of the inner ring members 130-7 and 130-8. In this case, the fixed resistor 190-1 having the resistance value of 1 Mohm may be installed in the inner ring member 130-7 having the thickness of 1 mm in FIG. 11(A) and the fixed resistor 190-2 having the resistance value of 10 Mohm may be installed in the inner ring member 130-8 having the thickness of 2 mm in FIG. 11(B).

Further, an outer ring member 110-5 may include a resistance measurement circuit 191 (for example, potentiometer, voltage divider, and the like) which may determine the resistance values of the fixed resistors 190-1 and 190-2 provided in the inner ring members 130-7 and 130-8.

Accordingly, when any one of the inner ring members 130-7 and 130-8 having different sizes (thicknesses or inner diameters) is coupled to the outer ring member 110-5, any one of terminals 190*a*-1 and 190*a*-2 of the fixed resistors 190-1 and 190-2 is coupled to a terminal 191*a* of the resistance measurement circuit 191. In this case, the resistance measurement circuit 191 detects the resistance values of the fixed resistor 190-1 and 190-2 and transmits the detected resistance values to the control unit (see 185 of FIG. 8).

The control unit 185 may control the power unit 180 with respect to a corresponding thickness of the inner ring member by determining the received detection signal and control the light-emitting intensity of the light-emitting part 172*a* by controlling a voltage applied to the light-emitting part 172*a*.

For example, the control unit 185 may control the light-emitting intensity of the light-emitting part 172*a* when the inner ring member 130-8 having the thickness of 2 mm is coupled to the outer ring member 110-5 to be larger than the light-emitting intensity of the light-emitting part 172*a* when the inner ring member 130-7 having the thickness of 1 mm is coupled to the outer ring member 110-5 and thus the control unit 185 may correct the sensing performance of the PPG sensor 172 according to the thicknesses of the inner ring members 130-7 and 130-8.

The fixed resistor is used as a method of detecting ring members having different thicknesses from each other in the embodiment, this is not limited thereto and various means may be used. As one example, when the inner ring member is coupled to the outer ring member, the user may directly control the light-emitting intensity of the light-emitting part 172*a* according to the thickness of the inner ring member. To this end, when the user inputs the thickness of the inner ring member to an application previously provided in the external device (see 20 of FIG. 13) through the external device 20, the input data may be transmitted to the control unit 185 in a wired or wireless manner. The control unit 185 may change the light-emitting intensity of the light-emitting part 172a by determining the data input from the external device 20. The GSR sensor 173 may detect current change due to moisture discharged from the finger skin. The skin humidity may be changed by the sympathetic nervous system and the GSR sensor 173 may detect the change of the skin humidity as change of the electrical resistance and thus provide the basis for determining whether or not to sleep such as arousal, drowsiness, and the like. It may determine whether or not to doze by simultaneously measuring a skin impedance response (SIR) corresponding to an alternating current component and an entire skin impedance level (SIL) corresponding to a direct current component, using a signal of the GSR sensor 173. When the user is dozing, the expression interval of the SIR may be increased, the expression frequency of the SIR may be reduced, and SIL may be increased.

The terminal 173a may be provided in the GSR sensor 173 and the terminal 173a of the GSR sensor 173 may be coupled to the inner ring member 130 to be electrically coupled to the skin contact terminal (see 173b of FIG. 13) which may be in direct contact with the skin. Such as a skin contact terminal 173b may be formed to have a size larger than the size of the terminal 173a of the GSR sensor 173 to improve the sensing performance of the GSR sensor 173 by increasing the contact area with the skin of the finger.

The ECG sensor 174 may be used to measure the ratio and consistency of the heartbeat as well as to check a size and a position of the heart and to check whether or not which damage is present in the heart. The ECG sensor 174 may be useful to measure and diagnose an abnormal rhythms of the heart and in particular, the ECG sensor 174 may be useful to measure the abnormal rhythms due to damage of the conduction tissue which transfers an electrical signal.

Figure 12:
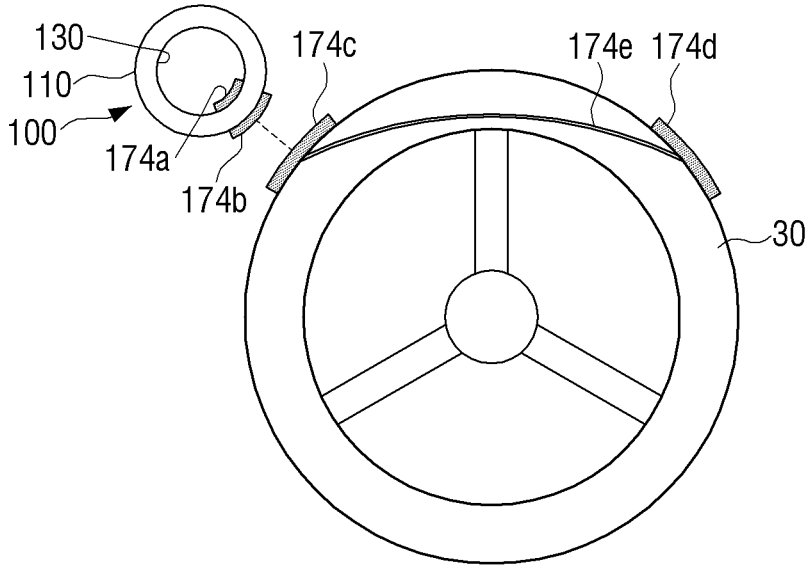
FIG. 12 is a schematic diagram illustrating an example of detecting the driver's drowsiness through an ECG sensor provided in a ring-type wearable device and a handle.

FIG. 12 is a schematic diagram illustrating an example of detecting the driver's drowsiness through an ECG sensor provided in a ring-type wearable device and a handle.

Referring to FIG. 12, a first terminal 174a which is disposed in the inner circumferential surface 130a of the inner ring member 130 to be in contact with the finger of the hand worn with the ring-type wearable device 100 and a second terminal 174b which is disposed in a portion of the outer ring member 110 (or a portion of the cover member 150) may be disposed in the ECG sensor 174. Further, a third terminal 174c which may be in electrical contact with the second terminal 174b may be disposed in one side of a handle 30 and a fourth terminal 174d may be disposed in the other side of the handle 30. The fourth terminal 174d may be in electrical contact with the third terminal 174c through a connection wiring 174e disposed in the inside of the handle 30.

To sense the drowsiness (or arousal state) of the driver, the driver grasps the one side of the handle 30 in a state that the ring-type wearable device 100 is worn in the finger of one hand (hereinafter, referred to as left hand) to allow the second terminal 174b of the ring-type wearable device 100 and the third terminals 174c to be in electrical contact with each other and grasps the other side of the handle 30 with the other hand (hereinafter, referred to as right hand) to allow the fourth terminal 174d and the right hand to be in contact with each other. The left hand is coupled to the first terminal 174a of the ECG sensor 174 and the right hand is coupled to the second terminal 174b of the ECG sensor 174 through the third and fourth terminals 174c and 174d and thus the condition that can measure the electrocardiogram of the driver is achieved.

In this case, the ECG sensor 174 may obtain electrocardiogram data by measuring a left channel signal in the first terminal 174a and a right channel signal in the second terminal 174b and determining a difference between electrical signals of the left and right hands. For example, the control unit 185 may determine that the driver is in a drowsiness state when an average of an R-R interval calculated by detecting an R peak among P, QRS, and T as main signals of the electrocardiogram is increased (in this case, the heart rate is slowed down). When it is detected that the driver is in a drowsiness state, the control unit 185 of the ring-type wearable device 100 may transmit a warning signal to a communication module (not shown) provided in a vehicle through the communication module 181 and a control unit (not shown) of the vehicle may receive the warning signal from a communication module of the vehicle and then generate a warning sound through a speaker and the like provided in the vehicle.

The control unit 185 may estimate the blood pressure of the user through the known method of estimating blood pressure through the electrocardiogram signal detected through the ECG sensor 174 and blood oxygen saturation detected through the PPG sensor 172.

The acceleration sensor 175 may detect a motion of the user and the control unit 185 may measure calorie consumption of the user through a signal detected through the acceleration sensor 175. The control unit 185 may detect the sleeping step of the user through the signal detected through the PPG sensor 172 or the ECG sensor 174 and the signal detected through the acceleration sensor 175. The acceleration sensor 175 may be replaced with a gyro sensor.

The temperature sensor 176 may be a non-contact temperature sensor and may measure a body temperature of the user or a temperature of an object. The temperature sensor 176 may be disposed in a position to be exposed to the outside of the ring-type wearable device 100, that is, a portion of an outer side of the outer ring member 110 or a portion of the outside of the cover member 150 to easily measure the temperature.

The fingerprint sensor 177 may be configured to detect the fingerprint of the user and may be disposed in a portion of the outer side of the outer ring member 110 or a portion of the outside of the cover member 150 to easily detect the fingerprint of the user similarly to the temperature sensor 176. The control unit 185 may perform a user authentication function using the signals detected through the fingerprint sensor 177 and the ECG sensor 174. In this case, the control unit 185 may perform the user authentication by comparing the detected fingerprint data and electrocardiogram data with fingerprint data and electrocardiogram data of the user previously stored in a memory.

The power unit 180 may receive power from the battery 182 and apply the power to the control unit 185 and the control unit 185 may control power supply to the sensor unit 171 and the communication module 181. The power unit 180 may include a pair of battery charge terminals 180a. In this case, the pair of battery charge terminals 180a may be exposed toward the inner side of the inner ring member 130 through openings (not shown) formed in the outer ring member 110 and the inner ring member 130 to be coupled to separate charge terminals (not shown). Further, the power unit 180 may include a wireless charge circuit (not shown)

and charge the battery power from a separate wireless charge device. In this case, the separate battery charge terminals 180a may be omitted.

Figure 13:
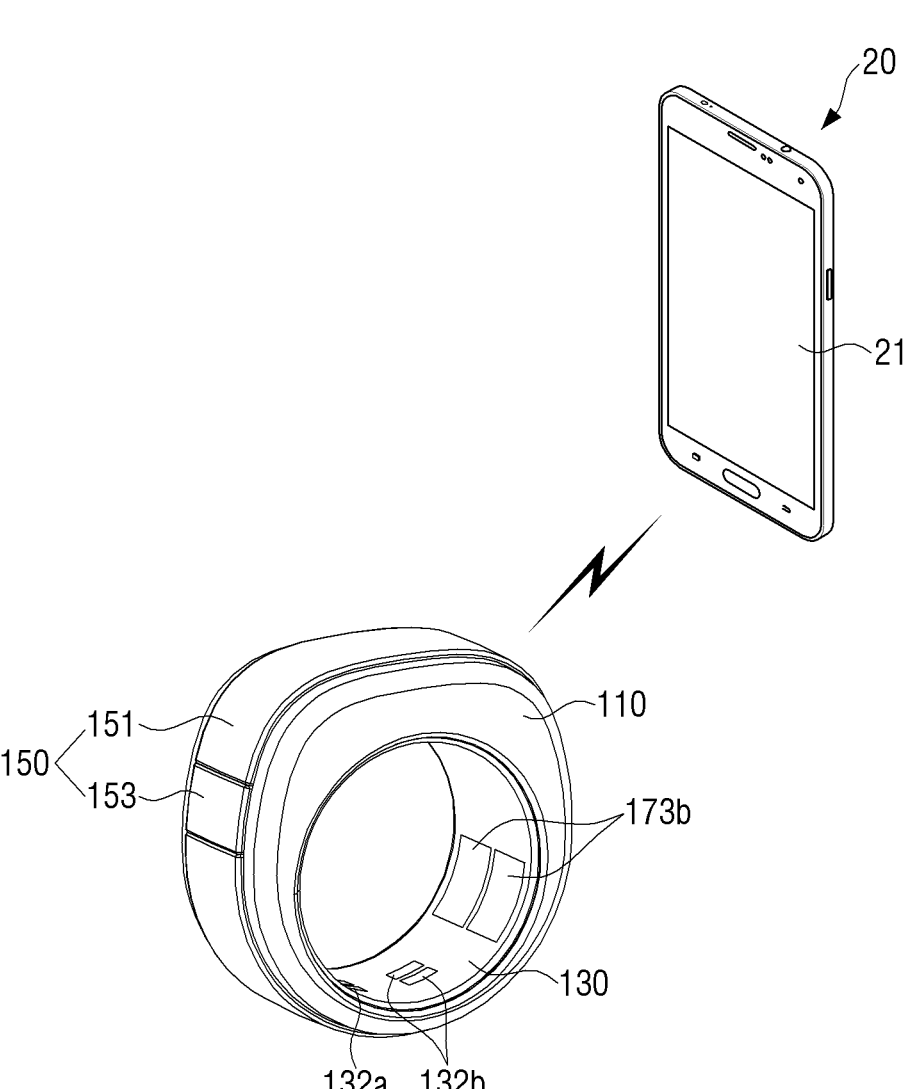
FIG. 13 is a schematic diagram illustrating an example which transmits and receives signals to and from an external device through a communication module.

FIG. 13 is a schematic diagram illustrating an example which transmits and receives signals to and from an external device through a communication module.

Referring to FIG. 13, the communication module 181 may transmit the various types of signals detected through the sensor unit 171 to the external device 20 and may also receive a signal transmitted from the external device 20.

The communication module 181 may include an element which performs at least one wireless communication function among Bluetooth, Wi-Fi, and Zigbee technologies. Further, the communication module 181 may include a near field communication (NFC) chip to implement a mobile payment function. In this case, the circuit unit 170 may include a circuit configured to perform a magnetic secure transmission (MST) payment method which supports a magnetic manner used in an existing plastic credit card in addition to the NFC method. In the case of performing the payment through the MST method, magnetic information generated in the ring-type wearable device 100 may be transmitted to a magnetic card payment terminal and the payment terminal may receive the magnetic information to perform the payment when the user authentication (security check) is performed through the fingerprint sensor 177 and then the ring-type wearable device 100 is brought near the magnetic card payment terminal.

Even in the payment using the NFC method, the user authentication may be performed and even when other payment methods other than the NFC and MST methods are applied to the embodiment, authentication means may be used.

The switch 183 may be a tactile switch as an analog switch. The button (see 183a of FIG. 7(B)) of the switch 183 may be pressed through the second part (see 153 of FIG. 2) of the cover member 150 and the switch 183 may turn on/off the power unit 180 or select a mode for performing various functions of the above-described ring-type wearable device 100, according to the number of times the button is pressed or the pressed time of the button.

Figure 14:
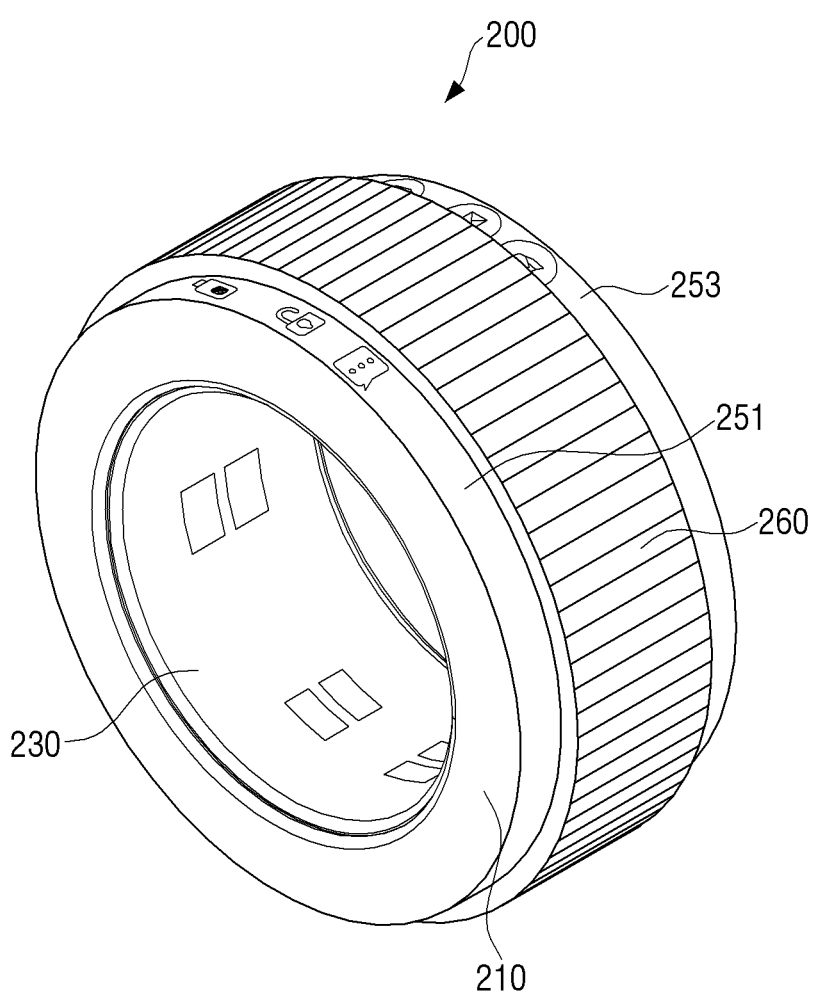
FIG. 14 is a perspective view illustrating a ring-type wearable device according to another embodiment of the present invention.

Although the above-described ring-type wearable device 100 displays the various biological information of the user according to the detected biological signal of the user through a display unit 21 of the separate external device 20, but this is not limited thereto and as illustrated in FIG. 14, a ring-type wearable device 200 may display various information through display units 251 and 253 provided in the ring-type wearable device 200 itself.

Figure 15:
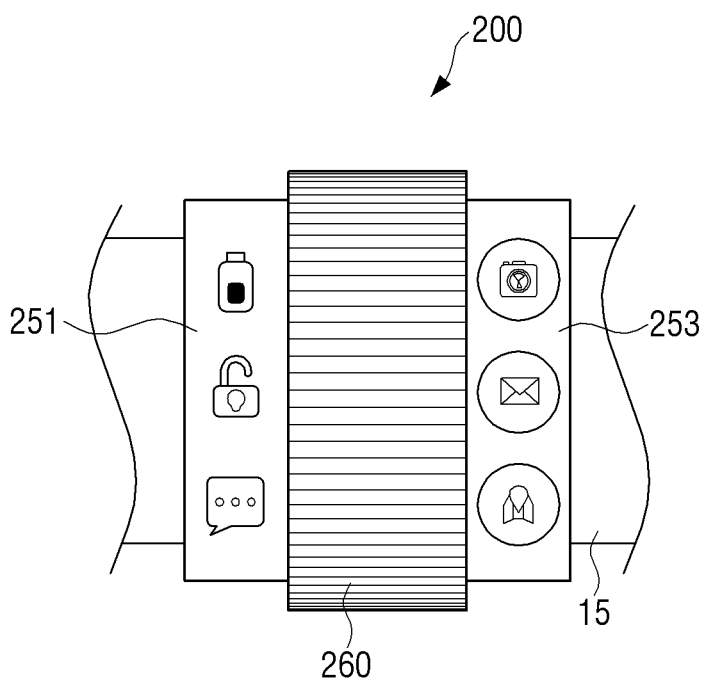
FIG. 15 is a plan view illustrating the ring-type wearable device illustrated in FIG. 14.

FIG. 14 is a perspective view illustrating a ring-type wearable device according to another embodiment of the present invention and FIG. 15 is a plan view illustrating the ring-type wearable device illustrated in FIG. 14.

Referring to FIG. 14, the configuration in the ring-type wearable device 200 according to another embodiment of the present invention is mostly the same as the configuration of the above-described ring-type wearable device 100. The configuration in the ring-type wearable device 200 is different from the configuration of the above-described ring-type wearable device 100 in that the ring-type wearable device 200 includes first and second display units 251 and 253 and a dial member 260 and in that the cover member 150 and the switch 183 are omitted in the ring-type wearable device 200. Accordingly, only the first and second display unit units 251 and 253 and the dial member 260 in the ring-type wearable device 200 according to another embodiment of the present invention which are different from the configuration of the above-described ring-type wearable device 100 will be described. The reference numeral 230 in FIG. 14 indicates the inner ring member.

Referring to FIG. 15, the first and second display units 251 and 253 may be disposed to a circumferential direction of an outer ring member 210 along the outer side of the outer ring member 210 with the dial member 260 interposed therebetween. Since the outer ring member 210 is formed to have a predetermined curvature, the first and second display units 251 and 253 may be flexibly configured to correspond to the outer ring member and may include a touch panel to input a touch input of the user.

The first and second display units 251 and 253 are electrically coupled to the control unit 185 and are controlled to display various information through the control unit 185. Herein, various information may be represented with a plurality of images (each image may be displayed with an icon having a predetermined shape) indicating functions implemented through the ring-type wearable device 200 or text.

The first and second display units 251 and 253 be operated to mutually react. For example, when one image displayed in the first display unit 251 is touched, a sub image (may be displayed with an icon having a predetermined shape) or predetermined text may be displayed in the second display unit 253 in response to the touch. Further, when an image displayed in any one of the first and second display units 251 and 253 is touched, a corresponding function may be performed.

Further, information displayed in the first and second display units 251 and 253 may be switched to each other through the control unit 185. The switching of the information between the first and second display units 251 and 253 may be performed by operating the switch 183 by the user or performed through a haptic function which can detect the motion through the acceleration sensor 175 by shaking the hand of the user worn with the ring-type wearable device 100 at predetermined speed.

Figure 16:
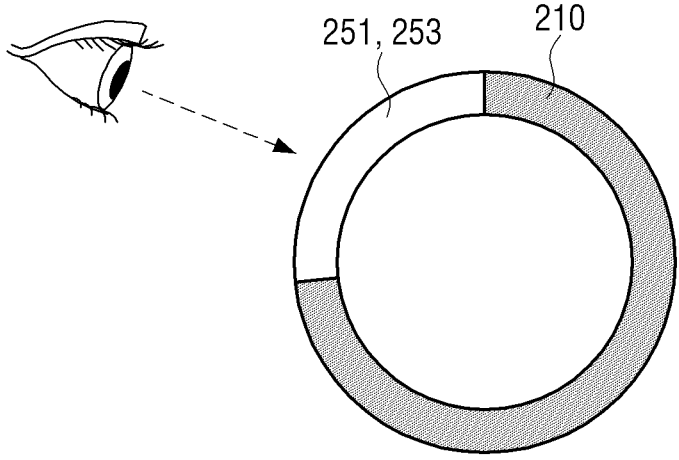
FIG. 16 is a schematic diagram illustrating an example that a display unit is limitedly installed in at least a portion of an outer ring member.

FIG. 16 is a schematic diagram illustrating an example that a display unit is limitedly installed in at least a portion of an outer ring member and FIG. 17 is a schematic diagram illustrating an example that a display region is changed to display information in a preset position when a ring-type wearable device is rotated.

Referring to FIG. 16, the first and second display units 251 and 253 may be installed only in a portion of the outer ring member 210.

Figure 17A:
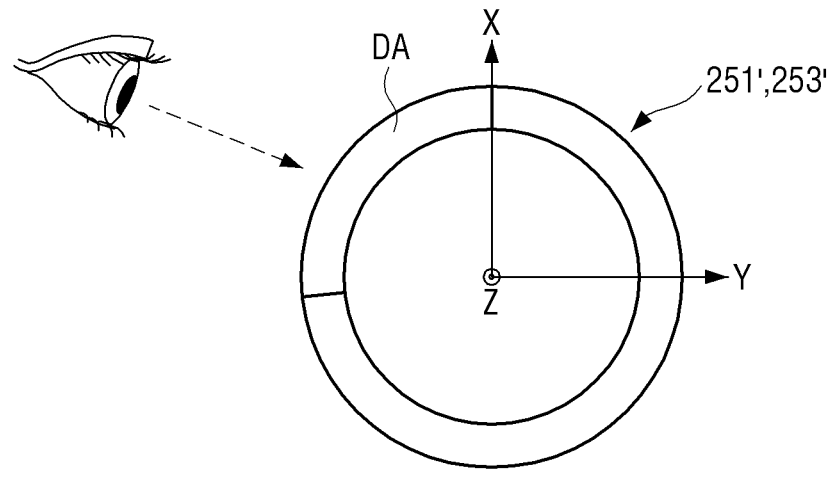
FIGS. 17A and 17B are schematic diagrams illustrating an example that a display region is changed to display information in a preset position when a ring-type wearable device is rotated.
Figure 17B:
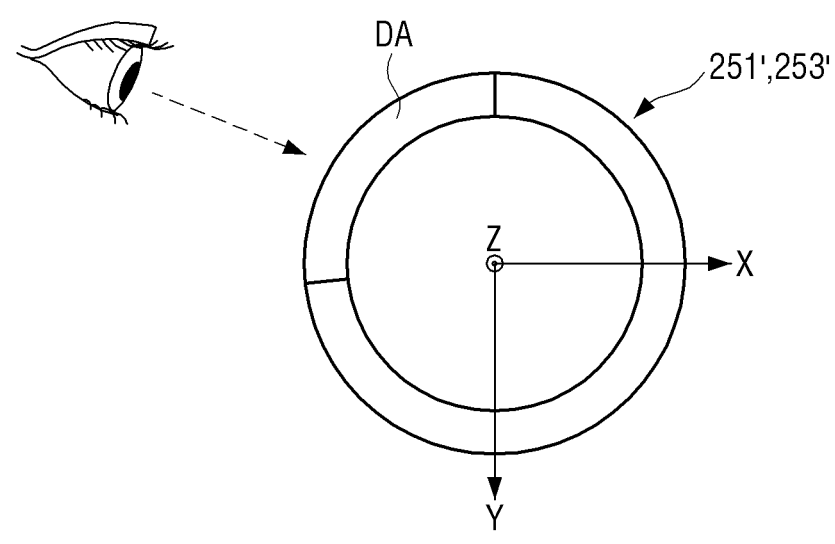

However, this is not limited thereto and the first and second display units 251 and 253 may be formed along the entire outer side of the outer ring member 210. In this case, as illustrated in FIG. 17(A), only a portion of an entire region of first and second display units 251' and 253' may be set to a display region DA which displays information. At this time, the display region DA may be displayed in a position corresponding to the user's eyes. When the ring-type wearable device is rotated to one direction, for example, 90 degrees on the basis of a center axis (this is, Z-axis) of the finger as illustrated in FIG. 17(B) in this state, the display region DA may be changed to a position that the ring-type wearable device rotates 90 degrees to a reverse direction of the rotation direction of the ring-type wearable device from the position before the ring-type wearable device is rotated and thus the display region may be intactly displayed in the position corresponding to the user's eyes. The change of the position in the display region may be implemented by detecting the rotation of the ring-type wearable device through the acceleration sensor (see 175 of FIG. 8), determining the detected signal through the control unit (see 185 of FIG. 8), and controlling the first and second display units 251' and 253' through the control unit.

Further, although it is described in the embodiment that two display units 251 and 253 are provided, but this is not limited thereto and only one display unit may be provided.

Referring back to FIG. 15, the dial member 260 may be rotatably installed in the outer ring member 210 and may select icons displayed in the first and second display units 251 and 253 in rotation to one direction and a reverse direction to the one direction. A sliding prevention protrusion may be formed along an outer circumferential surface of the dial member 260 to prevent slipping between the finger and the dial member 260 from being generated in rotation of the dial member 260. Further, the dial member 260 may be formed to have a larger outer diameter than the outer ring member 210 and thus the dial member 260 may be formed to protrude rather than the outer circumferential surface of the outer ring member 210. The user may easily rotate the dial member 260 through the structure of the above-described dial member 260.

Figure 18:
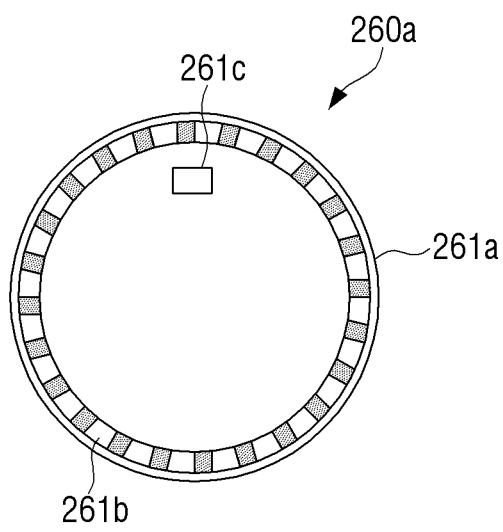
FIGS. 18, 19, and 20 are schematic diagrams illustrating various examples of a dial member illustrating in FIG. 14.
Figure 19:
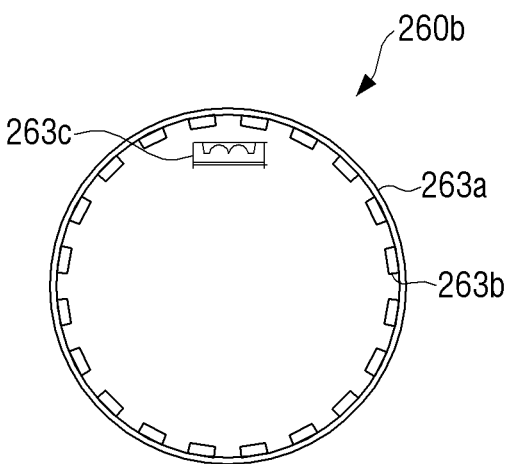
Figure 20:
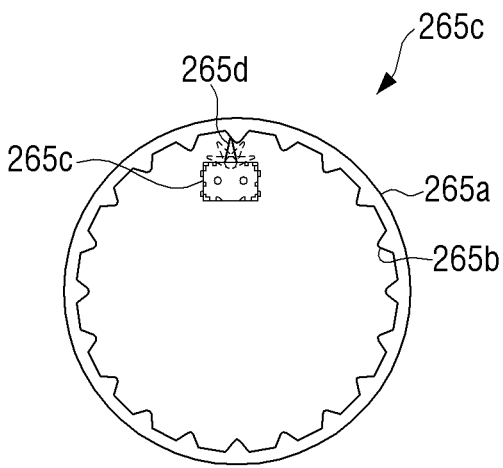

FIGS. 18 to 20 are schematic diagrams illustrating various examples of a dial member illustrating in FIG. 15.

Referring to FIG. 18, a dial member 260a may include a rotating body 261a forming an outside of the dial member 260a, a magnetic body 261b disposed along an inner circumferential surface of the rotational body 261a, and a hall sensor 261c configured to detect the magnetic body 261b.

The magnetic body 261b may be a magnetic strip attached along the rotating body 261a to alternately arrange an N pole and an S pole. The magnetic body 261b may rotate to the forward and reverse directions with the rotating body 261a and may be disposed along an entire section of an inner circumferential surface of the rotating body 261a. However, this is not limited thereto and the magnetic body 261b may be disposed in only a partial section of an inner circumferential surface of the rotating body 261a. When the magnetic body 261b is formed in the partial section of the rotating body 261a, the rotation angle of the rotating body 261a may be limited to be rotated by an angle range which can be detected through the hall sensor 261c.

The hall sensor 261c may be installed in a portion of the outer ring member 210 to face the magnetic body 261b at intervals. The hall sensor 261c may be electrically coupled to the control unit 185 and may detect polarity change of the rotating magnetic body 261b and transmit the detected signal to the control unit 185. The control unit 185 may calculate a rotation amount of the rotating body 261a and select an image arranged in a position corresponding to a rotation angle of the rotating body 261a among images displayed in the display units 251 and 253. In this case, cursor which moves to the same direction as the rotation direction of the rotating body 261a may be displayed in the display units 251 and 253.

Referring to FIG. 19, a dial member 260b may include a rotating body 263a forming an outside of the dial member 260b, a plurality of reflectors 263b arranged at the same interval along an inner circumferential surface of the rotational body 263a, and an image sensor 263c configured to detect the plurality of reflectors 263b.

The plurality of reflectors 263b may be disposed along an entire section of an inner circumferential surface of the rotating body 263a, but this is not limited thereto and the plurality of reflectors 263b may be disposed in only a partial section of an inner circumferential surface of the rotating body 263a. When the plurality of reflectors 263b are formed in the partial section of the rotating body 263a, the rotation angle of the rotating body 263a may be limited to be rotated by an angle range which can be detected through the image sensor 263c.

The image sensor 263c may be an optical encoder and may be installed in a portion of the outer ring member 210 to face the plurality of reflectors 263b at intervals. The image sensor 263c may detect the number of times light is reflected through the plurality of reflectors 263b in the rotation of the rotating body 263a and transmit the detected signal to the control unit 185. The control unit 185 may calculate a rotation amount (or rotation angle) of the rotating body 263a and select an image arranged in a position corresponding to a rotation angle of the rotating body 263a among images displayed in the display units 251 and 253. In this case, cursor which moves to the same direction as the rotation direction of the rotating body 263a may be displayed in the display units 251 and 253.

Referring to FIG. 20, a dial member 260c may include a rotating body 265a forming an outside of the dial member 260c, a plurality of protrusions 265b formed to protrude at the same interval along an inner circumferential surface of the rotational body 265a, and a switch 265c operated through the plurality of protrusions 265b.

The plurality of protrusions 265b may be disposed along an entire section of an inner circumferential surface of the rotating body 265a, but this is not limited thereto and the plurality of protrusions 265b may be disposed in only a partial section of an inner circumferential surface of the rotating body 265a. When the plurality of protrusions 265b are formed in the partial section of the rotating body 265a, the rotation angle of the rotating body 265a may be limited to be rotated by an angle range which can operate the switch 265c.

The switch 265c may be a two-way detection switch and may include a sensing protrusion 265d which are pushed through the plurality of protrusions 265b, which rotates to the forward and reverse direction together with the rotating body 265a, and rotates to one side or the other side. The switch 265c may be installed in a portion of the outer ring member 210 to maintain an interval that the sensing protrusion 265d can operate through the plurality of rotating protrusions 265b.

The switch 265c may detect the number of times and direction the sensing protrusion 265d is operated by the plurality of the protrusions 265b in the rotation of the magnetic body 265a and transmit the detected signal to the control unit 185. The control unit 185 may calculate a rotation amount (or rotation angle) of the rotating body 265a and select an image arranged in a position corresponding to a rotation angle of the rotating body 265a among images displayed in the display units 251 and 253. In this case, cursor which moves to the same direction as the rotation direction of the rotating body 265a may be displayed in the display units 251 and 253.

According to another embodiment of the present invention, the ring-type wearable device 200 may include its own display units 251 and 253 and display various body information based on the biological signal detected from the user in the display units 251 and 253 not through the separate external device 20.

The foregoing exemplary embodiments and advantages are merely exemplary and are not to be construed as limiting the present inventive concept. The description of the exemplary embodiments is intended to be illustrative, and not to limit the scope of the claims, and many alternatives, modifications, and variations will be apparent to those skilled in the art.

INDUSTRIAL AVAILABILITY

The present invention relates to a ring-type wearable device capable of detecting a biological signal of the user.

What is claimed is:

1. A ring-type wearable device comprising:
an outer ring;
an inner ring detachably inserted into an inner side of the outer ring;
a display disposed in the outer ring;
a sensor including a portion exposed towards an inside of the inner ring through a first opening in the outer ring and a corresponding second opening in the inner ring; and
a control circuit disposed in the outer ring,
wherein a size of the ring-type wearable device is changeable by replacing the inner ring with a different size.

2. The ring-type wearable device according to claim 1, wherein the sensor comprises a photo sensor including a light-emitter, and a light-receiver configured to receive light emitted from the light-emitter and reflected from an inside of a finger.

3. The ring-type wearable device according to claim 2, wherein the inner ring includes a lens configured to control a light radiation distance of the light-emitter and the lens is disposed in a position corresponding to the light-emitter and has a thickness corresponding to a thickness of the inner ring.

4. The ring-type wearable device according to claim 2, wherein the light-emitter is disposed in the second opening formed in the inner ring and elastically supported by the outer ring and a position of the light-emitter is based on a thickness of the inner ring.

5. The ring-type wearable device according to claim 2, further comprising:
a cover surrounding an outside of the outer ring;
wherein the control circuit is disposed in a space between the cover and the outer ring.

6. The ring-type wearable device according to claim 5, wherein the light-emitter is elastically supported by the cover and a position of the light-emitter varies is based on a thickness of the inner ring.

7. The ring-type wearable device according to claim 2, further comprising:
a fixed resistor having a resistance value corresponding to a corresponding thickness of the inner ring; and
a resistance measurement circuit configured to detect the resistance value of the fixed resistor,
wherein the control circuit is configured to control a light-emitting intensity of the light-emitter based on the resistance value detected through the resistance measurement circuit.

8. The ring-type wearable device according to claim 7, wherein the light-emitter is configured to emit a first light-emitting amount based on the inner ring having a first thickness and a second light-emitting amount larger than the first light-emitting amount based on the inner ring having a second thickness larger than the first thickness.

9. The ring-type wearable device according to claim 1, wherein the sensor includes a galvanic skin response (GSR) sensor and the inner ring includes a skin contact terminal electrically coupled to a terminal of the GSR sensor.

10. The ring-type wearable device according to claim 1, further comprising:
a dial rotatably coupled to an outer side of the outer ring and configured to operate the display.

11. The ring-type wearable device according to claim 10, wherein the display includes first and second displays disposed in a circumferential direction along both side surfaces of the outer ring based on the dial.

12. The ring-type wearable device according to claim 11, wherein the dial includes a rotating body configured to rotate in forward and reverse directions; a magnetic body configured to rotate with the rotating body and having N poles and S poles alternately arranged; and a hall sensor configured to detect polarity change of a magnetic pole of the magnetic body according to rotation of the rotating body, and
the control circuitry is configured to obtain a rotation amount of the rotating body through a sensing signal detected through the hall sensor.

13. The ring-type wearable device according to claim 11, wherein the dial includes a rotating body configured to rotate in forward and reverse directions; a plurality of reflectors configured to rotate with the rotating body and arranged at intervals; and an image sensor configured to receive light reflected from the plurality of reflectors according to rotation of the rotating body, and
the control circuit is configured to obtain a rotation amount of the rotating body through a sensing signal detected through the image sensor.

14. The ring-type wearable device according to claim 11, wherein the dial includes a rotating body configured to rotate in forward and reverse directions; a plurality of protrusions configured to protrude at intervals along an inner side of the rotating body; and a switch configured to operate through the plurality of protrusions according to rotation of the rotating body, and
the control circuitry is configured to obtain a rotation amount of the rotating body through a sensing signal detected through the switch.

15. The ring-type wearable device according to claim 5, wherein the outer ring further includes a communication circuit configured to wirelessly communicate with an external apparatus having a display; and
an antenna connected to the communication circuit disposed in an inner side of the cover, the antenna being configured of a non-metal material to transmit and receive signals to and from the external apparatus.

16. The ring-type wearable device according to claim 1, further comprising an electrocardiogram (ECG) sensor,
wherein the ECG sensor includes a first terminal exposed toward an inner side of the inner ring; and a second terminal exposed toward an outer side of the outer ring and electrically coupled to a hand not wearing the ring-type wearable device through a conductive handle.

17. The ring-type wearable device according to claim 5, wherein the cover, the outer ring and the inner ring each comprises a metal material.

18. The ring-type wearable device according to claim 5, further comprising an antenna disposed in the cover.

19. The ring-type wearable device according to claim 18, wherein a portion of the cover corresponding to the antenna comprises a non-metal material.

20. The ring-type wearable device according to claim 5, further comprising a battery disposed between the outer ring and the cover.

21. The ring-type wearable device according to claim 5, wherein the cover comprises a pressable portion configured to actuate a switch mounted on the control circuitry.

22. The ring-type wearable device according to claim 20, further comprising:
a charging terminal for charging the battery.

23. The ring-type wearable device according to claim 15, wherein the communication circuit is configured for Bluetooth wireless communication.

24. A ring-type wearable device comprising:

an outer ring;

an inner ring detachably inserted into an inner side of the outer ring;

a cover surrounding an outside of the outer ring;

a display disposed in the outer ring-a display disposed in the outer ring;

a battery disposed in a space between the outer ring and the cover;

a charging terminal for wired charging of the battery, the charging terminal exposed towards an inside of the inner ring through corresponding openings formed in the inner and outer rings; and control circuitry disposed in the space between the cover and the outer ring, wherein a size of the ring-type wearable device is changeable by replacing the inner ring with a different size.

\* \* \* \* \*